United States Patent
Ameri

(10) Patent No.: US 8,255,055 B2
(45) Date of Patent: Aug. 28, 2012

(54) MRI SHIELDING IN ELECTRODES USING AC PACING

(75) Inventor: Masoud Ameri, Maple Plain, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 390 days.

(21) Appl. No.: 12/367,457

(22) Filed: Feb. 6, 2009

(65) Prior Publication Data

US 2009/0204171 A1 Aug. 13, 2009

Related U.S. Application Data

(60) Provisional application No. 61/027,753, filed on Feb. 11, 2008.

(51) Int. Cl.
*A61N 1/00* (2006.01)

(52) U.S. Cl. .......... 607/36; 607/37; 607/116; 607/122

(58) Field of Classification Search ............ 607/36–37, 607/116, 122
See application file for complete search history.

(56) References Cited

U.S. PATENT DOCUMENTS

| | | |
|---|---|---|
| 5,003,975 A | 4/1991 | Hafelfinger et al. |
| 5,201,865 A | 4/1993 | Kuehn |
| 5,370,666 A | 12/1994 | Lindberg et al. |
| 5,476,485 A | 12/1995 | Weinberg et al. |
| 5,534,018 A | 7/1996 | Wahlstrand et al. |
| 5,549,646 A | 8/1996 | Katz et al. |
| 5,727,552 A | 3/1998 | Ryan |
| 5,727,553 A | 3/1998 | Saad |
| 5,755,742 A | 5/1998 | Schuelke et al. |
| 5,766,227 A | 6/1998 | Nappholz et al. |
| 5,800,496 A | 9/1998 | Swoyer et al. |
| 5,817,136 A | 10/1998 | Nappholz et al. |
| 5,861,013 A * | 1/1999 | Peck et al. ............... 607/28 |
| 5,891,179 A | 4/1999 | Er et al. |
| 6,016,447 A | 1/2000 | Juran et al. |
| 6,101,417 A | 8/2000 | Vogel et al. |
| 6,317,633 B1 | 11/2001 | Jorgenson et al. |

(Continued)

FOREIGN PATENT DOCUMENTS

EP 1852810 B1 11/2007

(Continued)

OTHER PUBLICATIONS

International Search Report and Written Opinion issued in PCT/US2009/056843, mailed Dec. 29, 2009, 13 pages.

(Continued)

*Primary Examiner* — Nicole F Lavert

(74) *Attorney, Agent, or Firm* — Faegre Baker Daniels LLP

(57) ABSTRACT

A medical device includes a pulse generator, an electrode configured to contact tissue in a coronary vessel, a lead comprising a lead conductor, the lead conductor connecting the pulse generator with the electrode, and a filter circuit electrically connected in series between the lead conductor and the electrode. The filter circuit may include a band pass filter that attenuates signals having a frequency other than a natural resonance frequency (e.g. MRI device signals), and the pulse generator may transmit therapy signals to the electrode as a sinusoidal voltage wave at the natural resonance frequency. The filter circuit may include a diode that rectifies the sinusoidal voltage wave before the rectified sinusoidal voltage wave passes to the electrode. In some embodiments, therapy signals may be provided to the electrode through the band pass filter over a natural resonance frequency range.

21 Claims, 2 Drawing Sheets

U.S. PATENT DOCUMENTS

| | | | |
|---|---|---|---|
| 6,721,600 B2 | 4/2004 | Jorgenson et al. | |
| 6,923,804 B2 * | 8/2005 | Eggers et al. | 606/34 |
| 6,949,929 B2 | 9/2005 | Gray et al. | |
| 6,999,818 B2 | 2/2006 | Stevenson et al. | |
| 7,013,180 B2 | 3/2006 | Villaseca et al. | |
| 7,047,075 B2 | 5/2006 | Stubbs | |
| 7,047,083 B2 | 5/2006 | Gunderson et al. | |
| 7,050,855 B2 | 5/2006 | Zeijlemaker et al. | |
| 7,113,827 B2 | 9/2006 | Silvestri et al. | |
| 7,123,013 B2 | 10/2006 | Gray | |
| 7,135,978 B2 | 11/2006 | Gisselberg et al. | |
| 7,138,582 B2 | 11/2006 | Lessar et al. | |
| 7,174,219 B2 | 2/2007 | Wahlstrand et al. | |
| 7,174,220 B1 | 2/2007 | Chitre et al. | |
| 7,239,916 B2 | 7/2007 | Thompson et al. | |
| 7,289,851 B2 | 10/2007 | Gunderson et al. | |
| 7,369,893 B2 | 5/2008 | Gunderson | |
| 7,388,378 B2 | 6/2008 | Gray et al. | |
| 7,535,363 B2 | 5/2009 | Gisselberg et al. | |
| 2003/0083726 A1 * | 5/2003 | Zeijlemaker et al. | 607/122 |
| 2003/0140931 A1 | 7/2003 | Zeijlemaker et al. | |
| 2003/0144705 A1 | 7/2003 | Funke | |
| 2003/0144718 A1 | 7/2003 | Zeijlemaker | |
| 2003/0144719 A1 | 7/2003 | Zeijlemaker | |
| 2003/0144720 A1 | 7/2003 | Villaseca et al. | |
| 2003/0144721 A1 | 7/2003 | Villaseca et al. | |
| 2003/0204217 A1 | 10/2003 | Greatbatch | |
| 2004/0064161 A1 | 4/2004 | Gunderson et al. | |
| 2005/0113676 A1 | 5/2005 | Weiner et al. | |
| 2005/0113873 A1 | 5/2005 | Weiner et al. | |
| 2005/0113876 A1 | 5/2005 | Weiner et al. | |
| 2005/0197677 A1 | 9/2005 | Stevenson | |
| 2005/0222656 A1 | 10/2005 | Wahlstrand et al. | |
| 2005/0222657 A1 | 10/2005 | Wahlstrand et al. | |
| 2005/0222658 A1 | 10/2005 | Hoegh et al. | |
| 2005/0222659 A1 | 10/2005 | Olsen et al. | |
| 2006/0030774 A1 | 2/2006 | Gray et al. | |
| 2006/0041294 A1 | 2/2006 | Gray | |
| 2006/0118758 A1 | 6/2006 | Wang et al. | |
| 2006/0247747 A1 | 11/2006 | Olsen et al. | |
| 2006/0247748 A1 | 11/2006 | Wahlstrand et al. | |
| 2006/0252314 A1 | 11/2006 | Atalar et al. | |
| 2006/0271138 A1 | 11/2006 | MacDonald | |
| 2007/0010702 A1 | 1/2007 | Wang et al. | |
| 2007/0027532 A1 | 2/2007 | Wang et al. | |
| 2007/0179577 A1 | 8/2007 | Marshall et al. | |
| 2007/0179582 A1 | 8/2007 | Marshall et al. | |
| 2007/0191914 A1 | 8/2007 | Stessman | |
| 2008/0033497 A1 | 2/2008 | Bulkes et al. | |
| 2008/0051854 A1 | 2/2008 | Bulkes et al. | |
| 2008/0132985 A1 | 6/2008 | Wedan et al. | |
| 2008/0154348 A1 * | 6/2008 | Atalar et al. | 607/116 |
| 2008/0208290 A1 | 8/2008 | Phillips et al. | |
| 2009/0005825 A1 | 1/2009 | Macdonald | |
| 2009/0024180 A1 | 1/2009 | Kisker et al. | |
| 2009/0149920 A1 | 6/2009 | Li et al. | |
| 2009/0149933 A1 | 6/2009 | Ameri | |
| 2009/0210022 A1 | 8/2009 | Powers | |
| 2010/0106215 A1 | 4/2010 | Stubbs et al. | |
| 2011/0087302 A1 | 4/2011 | Ameri | |
| 2011/0160816 A1 | 6/2011 | Stubbs et al. | |

FOREIGN PATENT DOCUMENTS

| | | | |
|---|---|---|---|
| WO | WO2010078552 A1 | 7/2010 | |

OTHER PUBLICATIONS

File History for U.S. Appl. No. 11/015,807, filed Dec. 17, 2004.
Basso, Christophe, "SPICE Model Simulates Spark-Gap Arrestor", Electronics Design, Strategy, and News (EDN), Jul. 3, 1997, 4 pages.
Partial International Search Report issued in PCT/US2011/052541, mailed Dec. 6, 2011, 4 pages.
International Search Report and Written Opinion issued in PCT/US2010/048620, mailed Apr. 5, 2011, 10 pagaes.

* cited by examiner

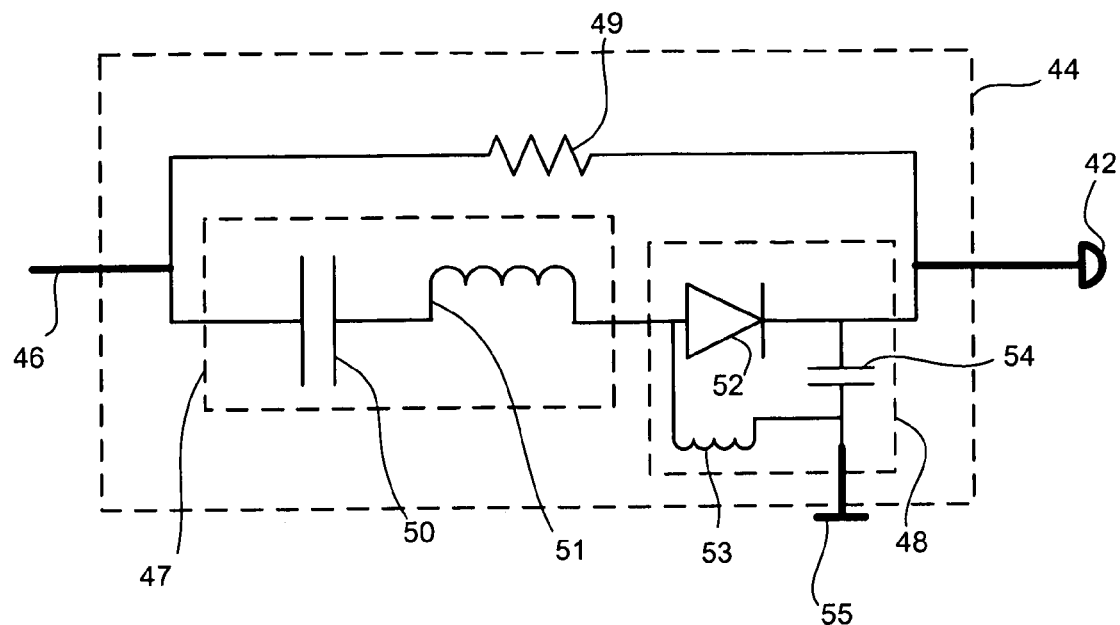
FIG. 2
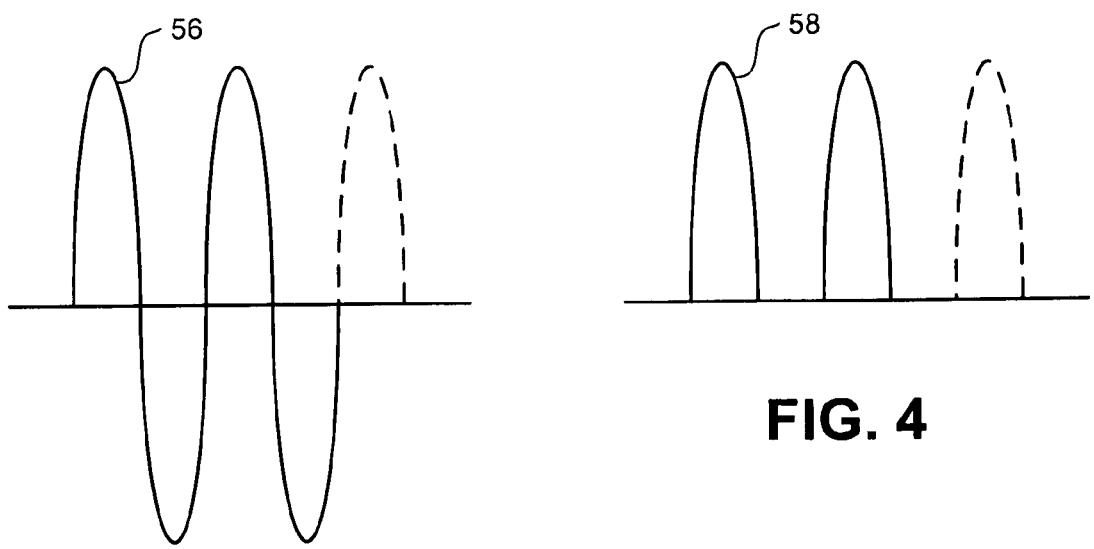
FIG. 3
FIG. 4

MRI SHIELDING IN ELECTRODES USING AC PACING

CROSS-REFERENCE TO RELATED APPLICATIONS

This application claims the benefit of U.S. Provisional Patent Application Ser. No. 61/027,753, filed on Feb. 11, 2008, and entitled, "MRI SHIELDING IN ELECTRODES USING AC PACING," which is incorporated by reference herein in its entirety for all purposes.

TECHNICAL FIELD

Embodiments of the present invention relate to medical devices and the simultaneous delivery of diagnostic and therapeutic treatments. More specifically, embodiments of the present invention relate to devices and methods for delivery of cardiovascular diagnostic or pacing therapy in a magnetic field environment.

BACKGROUND

Magnetic resonance imaging (MRI) is a non-invasive imaging method that utilizes nuclear magnetic resonance techniques to render images within a patient's body. Typically, MRI systems employ the use of a magnetic coil having a magnetic field strength of between about 0.2 to 3 Teslas. During the procedure, the body tissue is briefly exposed to RF pulses of electromagnetic energy in a plane perpendicular to the magnetic field. The resultant electromagnetic energy from these pulses can be used to image the body tissue by measuring the relaxation properties of the excited atomic nuclei in the tissue.

During imaging, the electromagnetic radiation produced by the MRI system may be picked up by implantable device leads used in implantable medical devices such as pacemakers or cardiac defibrillators. This energy may be transferred through the lead to the electrode in contact with the tissue, which may lead to elevated temperatures at the point of contact. The degree of tissue heating is typically related to factors such as the length of the lead, the conductivity or impedance of the lead, and the surface area of the lead electrodes. Exposure to a magnetic field may also induce an undesired voltage in the lead.

Accordingly, there is an ongoing need for devices and methods for shielding medical devices from magnetic fields during medical procedures such as magnetic resonance imaging (MRI).

SUMMARY

According to embodiments of the present invention, a filter circuit electrically connected in series between the lead conductor and the electrode includes a band pass filter which attenuates signals having a frequency other than a natural resonance frequency. According to such embodiments, the pulse generator transmits therapy signals to the electrode as a sinusoidal voltage wave at the natural resonance frequency. The band pass filter permits therapy voltage signals at the natural resonance frequency to pass through to the electrode, while blocking MRI-induced voltage signals which are at frequencies different from the natural frequency, according to embodiments of the present invention. The filter circuit may also include a rectifier circuit, such as a diode, to rectify the sinusoidal voltage wave at the natural frequency into a direct current signal for the electrode.

While some embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 2 is a schematic drawing of a filter circuit with a band pass filter connected in series between a lead conductor and an electrode, according to embodiments of the present invention.

FIG. 3 is a sinusoidal voltage diagram of a therapy signal sent from a pulse generator to an electrode, according to embodiments of the present invention.

FIG. 4 is a voltage diagram of the sinusoidal voltage diagram of FIG. 3 after diode rectification, according to embodiments of the present invention.

Figure 1:
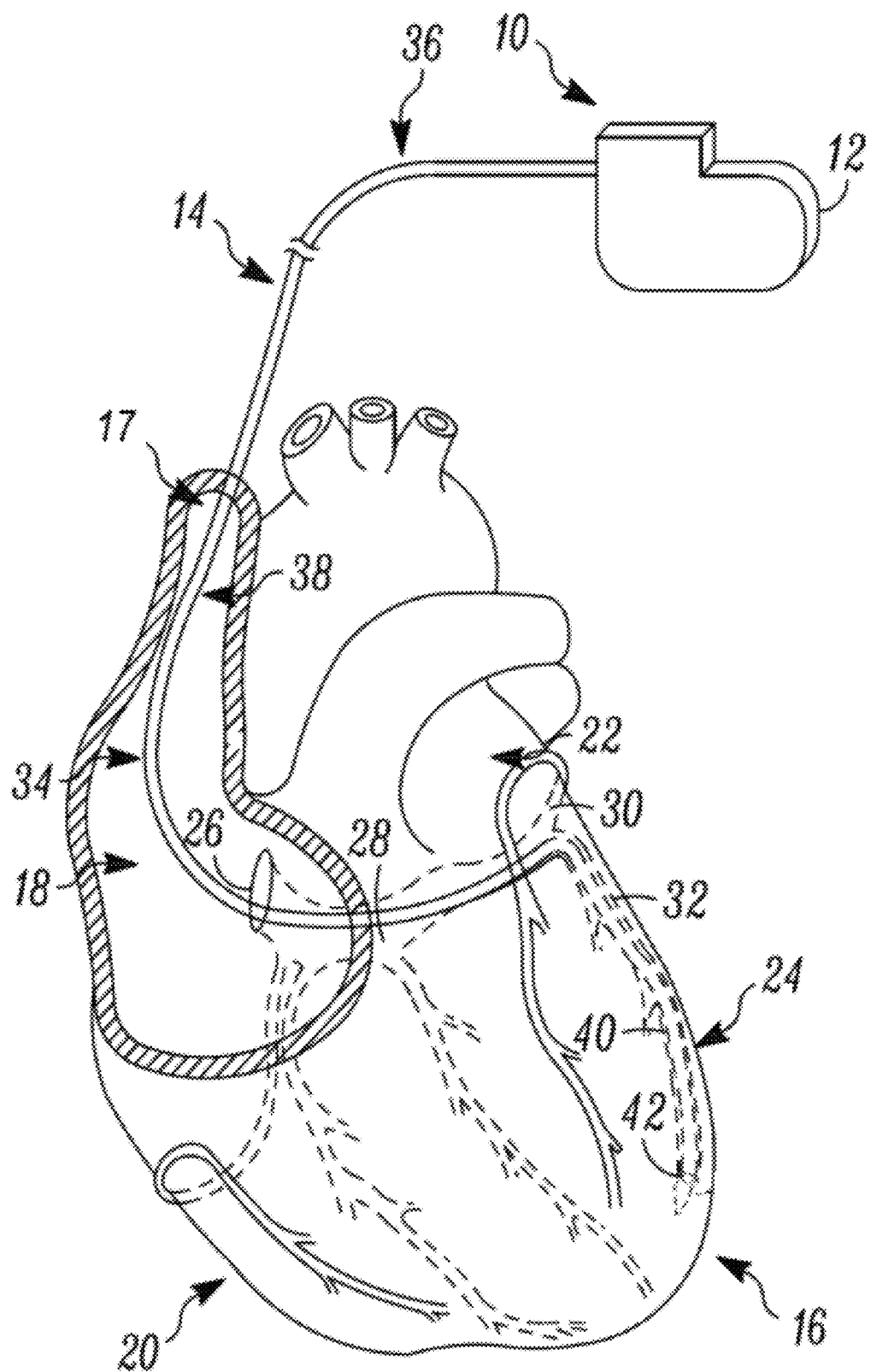
FIG. 1 is a schematic drawing of a cardiac rhythm management system including a pulse generator coupled to a lead deployed in a patient's heart, according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the appended claims.

DETAILED DESCRIPTION

FIG. 1 is a schematic drawing of a cardiac rhythm management system 10 including a pulse generator 12 coupled to a lead 14 deployed in a patient's heart 16 from a superior vena cava 17. As is known in the art, the pulse generator 12 is typically implanted subcutaneously at an implantation location in the patient's chest or abdomen. As shown, the heart 16 includes a right atrium 18 and a right ventricle 20, a left atrium 22 and a left ventricle 24, a coronary sinus ostium 26 in the right atrium 18, a coronary sinus 28, and various cardiac branch vessels including a great cardiac vein 30 and an exemplary branch vessel 32.

As shown in FIG. 1, the lead 14 may include an elongate body 34 including a proximal region 36 and a distal region 38. The distal region 38 has a distal end 40 including an electrode 42, according to embodiments of the present invention. The lead 14 includes a lead conductor which conductively connects the pulse generator 12 to the electrode 42, according to embodiments of the present invention. To facilitate left ventricular pacing epicardially via a transvenous approach, leads 14 may be deployed in coronary veins 32 through the coronary sinus 28. Although FIG. 1 depicts the lead 14 as part of a cardiac rhythm management system 10 with an electrode 42, the lead 14 may alternatively include one or more sensors and/or one or more electrodes 42, and may couple the one or more sensors with a monitor instead of and/or in addition to the pulse generator 12.

FIG. 2 illustrates a filter circuit 44 connected in series between a lead conductor 46 (which comprises part of lead 14) and an electrode 42, according to embodiments of the present invention. The filter circuit 44 includes a band pass filter 47 and a rectifier circuit 48, connected between the lead conductor 46 and the electrode 42, in parallel with a resistor 49, according to embodiments of the present invention. The band pass filter includes a capacitor 50 and an inductor 51 electrically connected in series, and the rectifier circuit 48 includes a diode 52 electrically connected in parallel with an inductor 53 and a capacitor 54, according to embodiments of the present invention. The filter circuit 44 may be used with multiple electrodes; for example, a ring electrode 55 may be electrically connected to the circuit 44 in addition to the electrode 42, which may be a tip electrode, according to embodiments of the present invention.

The band pass filter 47 attenuates (e.g. blocks) frequencies except for a natural resonance frequency, $f_0$. The natural resonance frequency $f_0$ in hertz may be found with the following equation:

$$f_0 = \frac{\sqrt{\frac{1}{LC}}}{2 \times \pi} \qquad \text{EQ. 1}$$

where L is the inductance of the inductor 51 in Henries, and C is the capacitance of the capacitor 50 in Farads. For filter circuits 44 which include a band pass filter 47 but which do not include a rectifier circuit 48 between the lead conductor 46 and electrode 42, the natural resonance frequency of the circuit 44 may be determined with (EQ. 1). When additional components are added between the band pass filter 47 and the electrode 42, such as, for example, inductor 53 and capacitor 54, the equation for calculating the natural resonance frequency of the circuit 44 changes. Based on the disclosure herein, one of ordinary skill in the art will recognize that the natural resonance frequency for any given circuit 44 may also be determined empirically through circuit 44 testing and/or simulation. As used herein, the term "band pass filter" is used in its broadest sense to refer to all circuitry between the lead conductor 46 and the electrode 42 that cooperates to attenuate signals passing through the circuit 44. Thus, although the band pass filter 47 of FIG. 2 is shown as including the capacitor 50 and the inductor 51, the band pass filter 47 may also include the components of the rectifier circuit 48, such that a natural resonance frequency of the band pass filter 47 is the natural resonance frequency of all such components, according to embodiments of the present invention.

According to some embodiments of the present invention, the band pass filter 47 attenuates signals at frequencies other than the natural resonance frequency by blocking such signals. According to other embodiments of the present invention, the band pass filter 47 attenuates signals at frequencies other than the natural resonance frequency by weakening such signals or reducing their amplitude without completely blocking them. According to some embodiments of the present invention, the band pass filter 47 attenuates signals at frequencies closer to the natural resonance frequency to a lesser degree than signals at frequencies further from the natural resonance frequency.

According to some embodiments of the present invention, a natural resonance frequency range exists. Signals in the natural resonance frequency range still have enough power to adequately provide therapy through the electrode 42 after passing through the band pass filter 47, but the natural resonance frequency range excludes frequencies at which signals are generated by an MRI system. According to such embodiments, the band pass filter 47 still substantially shields MRI signals between the lead conductor 46 and the electrode 42, while permitting transmission of therapy signals to the electrode 42 through the band pass filter 47 by a range of signal frequencies that are not exactly at the natural resonance frequency. Based on the disclosure provided herein, one of ordinary skill in the art will recognize that selection of such a natural resonance frequency range may depend on a number of factors, including hardware selection for the filter circuit 44 and therapy requirements.

When electromagnetic radiation from an MRI system is picked up by the implantable device leads 14, and more specifically by the lead conductor 46, the energy may be transferred through the lead conductor 46 and into the electrode 42, which is in contact with tissue, which may lead to elevated temperature at the point of contact. The induced voltage in the lead conductor 46 may also potentially disrupt the functionality of the pulse generator 12 and/or lead electrode 42. However, the radiofrequency energy of electromagnetic wave and lower frequency voltage induced by an MRI gradient field in the lead conductor 46 can be filtered out by using the filter circuit 44, and more specifically by using the band pass filter 47, according to embodiments of the present invention.

In some embodiments, resistor 49 is a high impedance resistor. As an example, the impedance of the resistor 49 is high enough to prevent electromagnetic energy picked up by the lead conductor 46 from transferring to the surrounding tissue via the electrode 42. However, the impedance of the resistor 49 is low enough to provide a conductive path between the pulse generator 12 and a common ground to permit sensing applications which might otherwise be inhibited by the inclusion of the band pass filter 47, at the electrode 42, according to embodiments of the present invention.

As illustrated in FIG. 3, the pulse generator 12 transmits therapy through the lead conductor 46 as a sinusoidal voltage signal 56 at the natural resonance frequency of the band pass filter 47. According to some embodiments of the present invention, the therapy voltage signal 56 is or operates as an alternating current (AC) signal. The band pass filter 47 permits the sinusoidal voltage signal 56 to pass through because its frequency matches or is substantially similar to the natural resonance frequency, while blocking the undesirable voltage signals created in the lead conductor 46 and/or electrode 42 by the MRI system because their frequencies do not match the natural resonance frequency. The rectifier circuit 48 rectifies the sinusoidal voltage signal 56 to form a rectified signal 58, as illustrated in FIG. 4, according to embodiments of the present invention. The rectified signal 58 is or operates as a direct current (DC) signal, according to embodiments of the present invention.

Although FIG. 2 depicts certain components comprising the band pass filter 47 and/or the rectifier circuit 48, one of ordinary skill in the art, based on the disclosure herein, will recognize that a variety of additional and other circuit layouts and components may be used for band pass filter 47 and/or rectifier circuit 48. For example, the band pass filter 47 may alternatively include a second, third, or fourth order filter configuration, or components and/or configurations that filter the signal at varying frequencies and/or in different ways. Various other rectifier circuits may also be used. Rectifier circuit 48 may include additional components that further condition the signal in addition to rectifying it, for example.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. A medical device, comprising:
   a pulse generator;
   an electrode configured to contact tissue in a coronary vessel;
   a lead comprising a lead conductor, the lead conductor connecting the pulse generator with the electrode; and
   a filter circuit electrically connected in series between the lead conductor and the electrode, the filter circuit comprising a band pass filter;
   wherein the band pass filter attenuates signals having a frequency other than a natural resonance frequency, and wherein the pulse generator transmits signals as a sinusoidal voltage wave at about the natural resonance frequency; and
   wherein the filter circuit further comprises a rectifier circuit, and wherein the rectifier curcuit rectifies the sinusoidal voltage wave before the rectified sinusoidal voltage wave passes to the electrodes.

2. The medical device of claim 1, wherein the rectifier circuit comprises a diode electrically connected in parallel with an inductor and a capacitor.

3. The medical device of claim 1, wherein the sinusoidal voltage wave operates as an alternating current signal, and wherein the rectified sinusoidal voltage wave operates as a direct current signal.

4. The medical device of claim 1, wherein the filter circuit further comprises a resistor electrically connected in parallel with the band pass filter.

5. The medical device of claim 4, wherein a resistance of the resistor shields electromagnetic energy received by the lead conductor from the electrode and creates a link between the lead conductor and the electrode to permit use of the electrode for sensing applications.

6. The medical device of claim 5, wherein the band pass filter comprises a capacitor and an inductor.

7. The medical device of claim 1, wherein the band pass filter comprises a capacitor and an inductor.

8. A medical device, comprising:
   an electrode configured to contact tissue in a coronary vessel;
   a lead comprising a lead conductor, the lead conductor electrically connecting to the electrode and configured to electrically connect to a pulse generator; and
   a filter circuit electrically connected in series between the lead conductor and the electrode, the filter circuit comprising a band pass filter;
   wherein the band pass filter attenuates signals having a frequency other than a natural resonance frequency, and wherein the lead conductor receives transmissions of signals from the pulse generator as a sinusoidal voltage wave at about the natural resonance frequency; and
   wherein the filter circuit comprises a rectifier circuit, and wherein the rectifier circuit rectifies the sinusoidal voltage wave before the rectified sinusoidal voltage wave passes to the electrode.

9. The medical device of claim 8, wherein the rectifier circuit further comprises a diode, and wherein the diode rectifies the sinusoidal voltage wave before the rectified sinusoidal voltage wave passes to the electrode.

10. The medical device of claim 9, wherein the sinusoidal voltage wave operates as an alternating current signal, and wherein the rectified sinusoidal voltage wave operates as a direct current signal.

11. The medical device of claim 8, wherein the filter circuit further comprises a resistor electrically connected in parallel with the band pass filter.

12. The medical device of claim 11, wherein a resistance of the resistor shields electromagnetic energy received by the lead conductor from the electrode and creates a link between the lead conductor and the electrode to permit use of the electrode for sensing applications.

13. The medical device of claim 8, wherein the band pass filter comprises a capacitor and an inductor.

14. A medical device, comprising:
    a pulse generator;
    an electrode configured to contact tissue in a coronary vessel;
    a lead comprising a lead conductor, the lead conductor electrically connecting the pulse generator with the electrode; and
    a filter circuit electrically connected in series between the lead conductor and the electrode, the filter circuit comprising a band pass filter;
    wherein the pulse generator is configured to transmit a signal to the electrode through the band pass filter at a frequency within a natural resonance frequency range of the band pass filter, and wherein the band pass filter is configured to shield the electrode from signals with frequencies outside of the natural resonance frequency range; and
    wherein the filter circuit further comprises a rectifier circuit, and wherein the rectifier circuit rectifies the signal from the pulse generator before the rectified signal passes to the electrode.

15. The medical device of claim 14, wherein the pulse generator is configured to transmit the signal to the electrode as a sinusoidal voltage wave.

16. The medical device of claim 15, wherein the rectifier circuit rectifies the sinusoidal voltage wave before the rectified sinusoidal voltage wave passes to the electrode.

17. The medical device of claim 16, wherein the rectifier circuit comprises a diode.

18. The medical device of claim 16, wherein the rectifier circuit comprises a diode electrically connected in parallel with an inductor and a capacitor.

19. The medical device of claim 14, wherein the filter circuit further comprises a resistor electrically connected in parallel with the band pass filter.

20. The medical device of claim 19, wherein a resistance of the resistor shields electromagnetic energy received by the lead conductor and creates a link between the lead conductor and the electrode to permit use of the electrode for sensing applications.

21. The medical device of claim 14, wherein the band pass filter comprises a capacitor and an inductor.

* * * * *

UNITED STATES PATENT AND TRADEMARK OFFICE
CERTIFICATE OF CORRECTION

PATENT NO.         : 8,255,055 B2
APPLICATION NO.    : 12/367457
DATED              : August 28, 2012
INVENTOR(S)        : Masoud Ameri It is certified that error appears in the above-identified patent and that said Letters Patent is hereby corrected as shown below:

Col. 5, Line 21: the term "electrodes" is amended to read "electrode[]"

Claim 6 is replaced with the following: "The medical device of claim 1, wherein the rectifier circuit comprises a diode."

Signed and Sealed this
Nineteenth Day of February, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,255,055 B2 | Page 1 of 1 |
| APPLICATION NO. | : 12/367457 | |
| DATED | : August 28, 2012 | |
| INVENTOR(S) | : Masoud Ameri | |

It is certified that error appears in the above-identified patent and that said Letters Patent is hereby corrected as shown below:

Col. 5, Line 21: the term "electrodes" is amended to read "electrode[]"

Col. 5, Lines 37-38, Claim 6 is replaced with the following: "The medical device of claim 1, wherein the rectifier circuit comprises a diode."

This certificate supersedes the Certificate of Correction issued February 19, 2013.

Signed and Sealed this
Nineteenth Day of March, 2013

Teresa Stanek Rea
*Acting Director of the United States Patent and Trademark Office*